United States Patent [19]

Kurek

[11] 4,380,677
[45] Apr. 19, 1983

[54] PREPARATION OF 2,6-DI-TERT-BUTYL-4-ALKYLPHENOLS

[75] Inventor: Paul R. Kurek, Schaumburg, Ill.

[73] Assignee: UOP Inc., Des Plaines, Ill.

[21] Appl. No.: 262,366

[22] Filed: May 11, 1981

[51] Int. Cl.$^3$ .................. C07C 39/06; C07C 37/11
[52] U.S. Cl. ................................ 568/788; 568/793
[58] Field of Search ........................ 568/788, 793

[56] References Cited

U.S. PATENT DOCUMENTS

| | | | |
|---|---|---|---|
| 2,733,274 | 1/1956 | Cowie | 568/788 |
| 2,802,884 | 8/1957 | D'Alelio | 568/788 |
| 3,037,052 | 5/1962 | Bortnick | 568/788 |
| 4,202,199 | 5/1980 | Marger et al. | 568/788 |
| 4,236,031 | 11/1980 | Dodd | 568/788 |
| 4,236,032 | 11/1980 | Dodd | 568/788 |
| 4,236,033 | 11/1980 | Alfs | 568/793 |

FOREIGN PATENT DOCUMENTS

| | | | |
|---|---|---|---|
| 692355 | 8/1964 | Canada | 568/788 |
| 953929 | 4/1964 | United Kingdom | 568/788 |

OTHER PUBLICATIONS

Rohm and Haas Company, "Liquid Process Chemical" Dept., No. 159, Aug. 1978, Special Issue, Philadelphia, Pa., Amberlite Ion Exchange Resins.
Pitochelli, "Ion Exchange Catalysis and Matrix Effects, Fluid Process Chemicals", Rohm & Haas, Philadelphia.

*Primary Examiner*—Werren B. Lone
*Attorney, Agent, or Firm*—James R. Hoatson, Jr.; Eugene I. Snyder; William H. Page, II

[57] ABSTRACT

Alkylation of 4-alkylphenols with 2-methylpropene in the presence of a macroreticular cation exchange resin bearing sulfonic acid groups with an internal surface area greater than about 200 $m^2/g$ and an average pore diameter less than about 120 Angstroms leads to the 2,6-dialkylated product in high yields. Using a resin with an internal surface area of from about 525 to about 575 $m^2/g$ and an average pore diameter from about 40 to about 60 Angstroms, there can be prepared from 4-methylphenol the antioxidant 2,6-di-tert-butyl-4-methylphenol in a yield in excess of 90%.

7 Claims, No Drawings

PREPARATION OF 2,6-DI-TERT-BUTYL-4-ALKYLPHENOLS

Alkylated phenols as a group long have been known to exhibit outstanding antioxidant properties. Among these, the titled compounds are prime examples, having an outstanding history as food additives to retard oxidative deterioration and spoilage.

Because of their utility, the preparation of the titled phenols in general, and 2,6-di-tert-butyl-4-methylphenol (BHT) in particular, have been subjected to unusual scrutiny. Broadly described, these materials have been prepared by reacting a phenol with an alkylating agent in the present of an alkylation catalyst. Olefins frequently have been used as the alkylating agent and often are preferred over alternative alkylating agents, for example, alkyl halides, alcohols, and esters.

Virtually all alkylating catalysts share the property of being Lewis acids. Within the class of Lewis acids, mineral acids frequently have been used as alkylating agents, and among these sulfuric acid has been broadly adopted in alkylation methods. The organic counterparts of sulfuric acid, the sulfonic acids, also have been successfully employed as alkylating catalyts, as exemplified by the process for preparing BHT as described in U.S. Pat. No. 2,733,274.

With the advent of synthetic cation exchange resins bearing aliphatic acid groups there become available methods of alkylating phenols using a solid catalyst. Thus, U.S. Pat. No. 2,802,884 describes the alkylation of aromatic hydroxy compounds with olefins using sulfonated divinyl aryl and phenol-formaldehyde resins as a catalyst. It is there stated that using the method as claimed leads to BHT from 4-methylphenol and 2-methylpropene in a yield of about 42%. This pioneer patent perforce describes only the use of gelular, or microreticular, resins since macroreticular resins then were unknown. By macroreticular resins are meant resins of a sponge-like structure having large discrete pores, in contrast to microreticular resins which are of a denser, more compact structure generally requiring swelling by solvent to be effective.

Subsequently, U.S. Pat. No. 3,037,052 disclosed the use of a macroreticular cation exchange resin, namely, a sulfonated, cross-linked styrene-divinylbenzene, in the alkylation of phenols. The patentee showed such resins were several fold more active as catalysts than analogous microreticular resins, but there was no showing of increased selectivity or yield in the dialkylation of an alkyl phenol. However, such an increase is shown in U.S. Pat. No. 4,202,199 where the patentee claims a microreticular cation exchange resin can afford BHT in 87% yield from 4-methylphenol and 2-methylpropene in a stirred reactor so long as the particles of resin are in the range of 10 to 200 micrometers. The selectivity characteristics of macroreticular resins are dramatically demonstrated in U.S. Pat. Nos. 4,236,031 and 4,236,032, where monoalkylation of 2,3-dimethylphenol or 3-methylphenol using 2-methylpropene and a macroreticular ion exchange resin occurs with great selectivity at the 6-position at a temperature from 50° to 90° C., and at the 5-position when the temperature is in excess of 100° C.

Thus, the prior art discloses methods of alkylating phenols with olefins using cation exchange resins as the alkylation catalyst. Although some of the art ascribes advantages to microreticular resins while other art ascribes advantages to macroreticular resins, none of the art distinguishes amongst the various types of macroreticular resins. In particular, the prior art fails to show the use of macroreticular resins as a catalyst in the dialkylation of an alkylated phenol with high yield and selectivity, and is silent regarding a difference in effectiveness amongst macroreticular resins as alkylation catalysts.

A discovery leading to this invention is the observation that macroreticular cation exchange resins having sulfonic acid groups exhibit substantial differences in properties as a catalyst in the alkylation of 4-alkylphenols with olefins. In particular, it has been observed that different macroreticular resins lead to widely divergent results in the alkylation of 4-alkylphenols with 2-methylpropene, and only certain of these resins lead to dialkylation in high yield and selectivity. More particularly, a critical feature of this invention is the observation that the use of such resins with relatively high surface area and relatively low average pore size leads to substantially higher yields of BHT in the reaction of 4-methylphenol with 2-methylpropene than heretofor possible.

SUMMARY

An object of this invention is to provide a method of preparing 2,6-di-tert-butyl-4-alkylphenols in high yield by alkylating 4-alkylphenols with 2-methylpropene. An embodiment of this invention is a process wherein alkylation is performed in the presence of an alkylating catalyst which is a macroreticular cation exchange resin bearing sulfonic acid groups with an internal surface area greater than about 200 $m^2/g$ and an average pore diameter less than about 120 Angstroms. In a more specific embodiment the reactant phenol is 4-methylphenol, the resin has an internal surface area from about 525 to about 575 $m^2/g$, and an average pore diameter from about 40 to about 60 Angstroms.

DESCRIPTION OF THE INVENTION

The invention described herein is a method of preparing 2,6-di-tert-butyl-4-alkylphenols in high yields by reacting a 4-alkylphenol with 2-methylpropene in the presence of an alkylating catalyst. More particularly, this invention relates to a method of alkylation wherein the alkylating catalyst is a macroreticular cation exchange resin bearing sulfonic acid groups. This invention is grounded on the observation, previously unknown, that such resins are peculiarly effective alkylating agents when the resins have an internal surface area greater than about 200 $m^2/g$ and an average pore diameter less than 120 Angstroms. Application of the method described herein affords yields of 2,6-di-tert-butyl-4-methylphenol in excess of 90% without recycling, a result far surpassing prior described methods of preparing said phenol.

The method described herein may be applied to any 4-alkylphenol. The nature of the alkyl group does not pose a limitation, so long as the alkylphenol is not larger than the pore opening, and the alkyl group may be either branched or unbranched. Examples of suitably alkyl groups include methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl. The preferred alkyl groups contain 1 to 4 carbon atoms with methyl being especially preferred.

The phenol is reacted with at least three molar proportions of 2-methylpropene, and generally with not more than 10 molar proportions. It has been found that the use of at least 4 to 5 molar proportions of this olefin affords the desired dialkylation product in a yield of at least 90%. In a preferred mode of this invention, from about 4 to about 8 molar proportions of 2-methylpropene are used.

The phenol is reacted with 2-methylpropene in the presence of a macroreticular cation exchange resin bearing sulfonic acid groups as the alkylating catalyst. It is critical to the success of this invention that the resin have an internal surface area greater than about 200 m$^2$/g and an average pore diameter less than about 120 Angstroms. A surface area from about 200 to about 600 m$^2$/g is preferred, with the range from about 525 to about 575 m$^2$/g especially preferred. An average pore diameter from about 30 to about 120 Angstroms is preferred, with a range from 30 to about 80 Angstroms more preferred, and the range from about 40 to about 60 Angstroms especially preferred.

The method of this invention may be performed as a batch process or as a continuous process, for example, using a fixed bed. When performed in a batch manner, some mixing is desirable to ensure adequate contact between all reactants and the catalyst. In a typical batch reaction, the 4-alkylphenol and the resin are introduced into an autoclave. The amount of resin used affects both the reaction temperature and time. It is generally desired to use the minimum amount of catalyst consistent with a reasonable reaction time at a given temperature. It is convenient, although not critical, to use from about 1 to about 40 grams of resin per mole of phenol. The desired amount of 2-methylpropene is introduced, and if it is desired to conduct a reaction at a pressure other than autogeneous pressure, a suitable inert gas is introduced, such as nitrogen or argon. Generally, a pressure less than about 150 psig will suffice. It is also possible to use nonreactive solvents in which to conduct the alkylation.

After the reactants and catalyst are introduced to the reactor, the mixture is brought to reaction temperature. Alkylation is performed at a temperature from about 50° to about 125° C., with the range from about 100° to about 120° C. being preferred. The reaction time will vary inversely with the temperature, but a time from about 4 to about 6 hours at a temperature in the range from about 100° to 110° C. is typical. After the reaction is complete, the product 2,6-di-tert-butyl-4-alkylphenol is recovered simply by separating the solid resin, as by filtration, and distilling the excess olefin and/or solvent. The resin which is recovered by filtration may be recycled without appreciable change in results.

The examples given below are intended merely to illustrate this invention and are not intended to limit it thereto.

EXAMPLE 1

Into a 300 cc stirred autoclave was charged 43.2 g (0.4 mol) 4-methylphenol, 112 g (2.0 mol) 2-methylpropene, and 10 g of a macroreticular cation exchange resin bearing sulfonic acid groups. The resin used was obtained from Rohm and Haas and is a highly cross-linked polystyrene-divinylbenzene resin with an internal surface area of about 540 m$^2$/g and an average pore size of about 51 Angstroms. The resin had been "conditioned" by use in a prior alkylation, which was found desirable for consistent, predictable results.

The mixture was stirred at 100° C. for 6 hours at pressures from about 25 to about 100 psig. After the mixture had cooled, it was removed from the autoclave and filtered to remove the resin. The resin cake and autoclave were rinsed with acetone which was then combined with the filtrate. The latter was stripped of solvent at 50° C. at reduced pressure to afford a product consisting of about 94% 2,6-di-tert-butyl-4-methylphenol and 9% 2-tert-butyl-4-methylphenol. About 99% of reactant was converted to product.

EXAMPLE 2

This experiment was run substantially similar to that of Example 1 except that the resin used was AMBERLYST 15 ™ supplied by Rohm and Haas. This resin is also a macroreticular, highly cross-linked polystyrene-divinylbenzene bearing sulfonic acid groups but with a surface area of only about 45 m$^2$/g and an average pore diameter of about 265 Angstroms. It was not found necessary to condition this resin as was described in the prior example. Use of this resin afforded 99% conversion of reactant phenol to a product comprising 27% 2,6-di-tert-butyl-4-methylphenol and 68% 2-tert-butyl-4-methylphenol.

Comparison of Examples 1 and 2 shows the enormous beneficial effect upon yield of BHT accompanying use of a macroreticular resin with high surface area and relatively low average pore diameter.

EXAMPLES 3–6

In these examples a mixture of 4-methylphenol and the resin in Example 1 (25 g per mole phenol) were reacted at 100° C. and 25–100 psig for 6 hours with various mole ratios 2-methylpropene according to the procedure of Example 1. The yield of BHT versus mole ratio olefin is tabulated below:

| Example | Mole ratio olefin:phenol | Percent yield BHT |
|---|---|---|
| 3 | 0.5 | 8 |
| 4 | 1.0 | 22 |
| 5 | 2.5 | 30 |
| 6 | 5.0 | 94 |

The BHT yield does not appear to increase appreciably at a mole ratio greater than about 5. In contrast to these results, use of Amberlyst 15 ™ at 85° C. and 25 psig showed the yield of BHT attained a maximum of an olefin:phenol mole ratio of about 2.

What is claimed is:

1. A method of preparing a 2,6-di-tert-butyl-4-alkylphenol comprising reacting a 4-alkylphenol with from about 3 to about 10 molar proportions of 2-methylpropene at a temperature from about 50° to about 125° C. in the presence of a macroreticular cation exchange resin bearing sulfonic acid groups, said resin having an internal surface area from about 200 to about 600 m$^2$/g with an average pore diameter from about 30 to about 120 Angstroms, and recovering the 2,6-di-tert-butyl-4-alkylphenol produced thereby.

2. The method of claim 1 where the phenol is 4-methylphenol.

3. The method of claim 1 where said resin has an internal surface area from about 525 to about 575 m$^2$/g.

4. The method of claim 1 where said resin has an average pore diameter from about 30 to about 80 Angstroms.

5. The method of claim 4 where the pore diameter is from about 40 to about 60 Angstroms.

6. The method of claim 1 where the molar proportion of 2-methylpropene is from about 4 to about 8.

7. The method of claim 1 where the temperature is from about 100° to about 120° C.

* * * * *